United States Patent [19]
Jirousek et al.

[11] Patent Number: 5,962,446
[45] Date of Patent: Oct. 5, 1999

[54] THERAPETUTIC TREATMENT FOR HUMAN T CELL LYMPHOTROPHIC VIRUS TYPE 1 INFECTION

[75] Inventors: Michael R. Jirousek; Douglas Kirk Ways; Lawrence E. Stramm, all of Indianapolis, Ind.

[73] Assignee: Eli Lilly and Company, Indianapolis, Ind.

[21] Appl. No.: 08/917,517

[22] Filed: Aug. 26, 1997

Related U.S. Application Data

[60] Provisional application No. 60/024,938, Aug. 30, 1996.

[51] Int. Cl.$^6$ .................................................. A61K 31/395
[52] U.S. Cl. .................. 514/183; 424/187.1; 424/207.1; 514/2; 514/185
[58] Field of Search .............................. 424/187.1, 207.1; 435/235.1, 236; 514/2, 8, 183, 185; 530/300

[56] References Cited

U.S. PATENT DOCUMENTS

| | | |
|---|---|---|
| 5,057,614 | 10/1991 | Davis et al. . |
| 5,063,238 | 11/1991 | Sunkara et al. .......................... 514/340 |
| 5,380,746 | 1/1995 | Barth et al. .............................. 514/414 |
| 5,481,003 | 1/1996 | Gillig et al. . |
| 5,491,242 | 2/1996 | Gillig et al. . |
| 5,516,915 | 5/1996 | Barth et al. .............................. 548/455 |
| 5,545,636 | 8/1996 | Heath et al. . |
| 5,552,396 | 9/1996 | Heath et al. . |
| 5,621,098 | 4/1997 | Heath et al. . |

FOREIGN PATENT DOCUMENTS

| | | |
|---|---|---|
| 0 657 411 A1 | 2/1994 | European Pat. Off. . |
| 0 657 458 A1 | 6/1995 | European Pat. Off. . |
| WO 94/14798 | 7/1994 | WIPO . |

OTHER PUBLICATIONS

Lindholm, et al., "Human T–Cell Lymphotrophic Virus Type 1 $Tax_1$ Activation of NF–κB: Involvement of the Protein Kinase C Pathway," J. Virol., vol. 70, No. 4, 2525–2532, 1996.

Daniela Saggioro et al. "Tax–Induced HTLV–1 LTR Transcriptional Activation is Modulated by Phosphorylation" Biochemical and Biophysical Research Communications, vol. 205, No. 1, Nov. 30, 1994, pp. 666–673.

Sandra E. Wilkinson et al. "Isoenzyme specificity of bisindolylmaleimides, selective inhibitors of protein kinase C" Biochem J. (1993) 294 pp. 335–337.

Adchi et al., Biochem. Biophys. Res. Commun. 169: 469–475, 1990.

Arima et al., J. Virology 65: 6892–6899, 1991.

H. Bundgaard, *Design of Prodrugs*, (1985).

Gessain et al., Lancet II: 407–410, 1985.

Hinuma et al., PNAS 78: 6476–6480, 1981.

Jensen et al., J. Virology 66: 4427–4433, 1992.

Leung et al., Nature 333: 776–778, 1988.

Lindholm et al., New Biol. 2: 1034–1043, 1990.

Lindholm et al., J. Virology 70: 2525–2532, 1996.

Osame et al., Lancet I: 1031–1032, 1986.

Poiesz et al., PNAS 77: 7415–7419, 1980.

Smith et al., J. Clin. Invest. 87: 761–766, 1991.

Tan et al., Mol. Cell. Biol. 9: 1733–1745, 1989.

Yoshimura et al., EMBO J 9: 2537–2542, 1990.

*Primary Examiner*—Robert D. Budens
*Attorney, Agent, or Firm*—Paul R. Darkes

[57] ABSTRACT

A method for treating human T cell lymphotrophic virus type 1 infection using an isozyme selective PKC inhibitor, particularly using the isozyme selective PKC inhibitor, (S)-3,4-[N,N'-1,1'-((2"-ethoxy)-3'"(O)-4'"-(N,N-dimethylamino)-butane)-bis-(3,3'-indolyl)]-1(H)-pyrrole-2, 5-dione hydrochloride salt.

27 Claims, No Drawings

THERAPETUTIC TREATMENT FOR HUMAN T CELL LYMPHOTROPHIC VIRUS TYPE 1 INFECTION

This application claims the priority benefits of the U.S. Provisional application Ser. No. 60/024,938 filed Aug. 30, 1996.

BACKGROUND OF THE INVENTION

1. Field of the Invention

The present invention is broadly directed to a method for treating human T cell lymphotrophic virus type 1 (HTLV-1) infection. In particular, the invention is directed to a method for inhibiting the induced effects of HTLV-1 viral protein activity such as Tax 1 activity and for inhibiting replication of HTLV-1. The present invention is particularly directed to the use of a particular class of isozyme selective Protein Kinase C (PKC) inhibitors for treating HTLV-1 infection and the diseases associated therewith such as T cell leukemia and HTLV-1 induced central nervous system disorder.

2. Description of Related Art

People infected with human T cell lymphotrophic virus type 1 (HTLV-1) are prone to developing adult T cell leukemia. In addition, HTLV-1 infected individuals can manifest chronic neurodegenerative illnesses such as tropical spastic paraparesis and myelopathy. No particular treatment for HTLV-1 infection is available in the art. Treatment for diseases associated with HTLV-1 infection is symptomatic and does not provide satisfactory results. Therefore, there remains a need in the art to develop therapeutic agents for treatment of HTLV-1 infection and the diseases associated therewith.

Leukemia is a disease characterized by neoplastic proliferation of one of the blood-forming cells. The different types of leukemia are classified according to the cell type involved, and as acute or chronic, depending on the duration of the disease. If left untreated, all forms of leukemia are fatal. Death is usually due to complications resulting from infiltration of the bone marrow by leukemic cells and replacement of normal hematopoietic cells. Adult T cell leukemia may be associated with HTLV-1 infection. During the last quarter century, a worldwide effort has been mounted to improve the treatment of leukemia. Using the best current treatment regimens, over 90 percent of children with acute lymphoblastic leukemia (ALL) now achieve complete remission. However, adults with ALL, especially T cell leukemia, generally respond less favorably to treatment than children, and most trials have resulted only in complete remission rates of 50 percent or less, and only with a median duration of a year or less. Therefore, there is a continuing need in the art to develop new therapeutic agents for treatment of adult T cell leukemia associated with HTLV-1 infection.

HTLV-1 infection also can cause chronic neurodegenerative disorders. Chronic neurodegenerative illnesses such as tropical spastic paraparesis and myelopathy may cause loss of function, suppression of reflex activity, and other complications. In general, the treatment for neurodegenerative disorders is conservative and symptomatic without complete recovery. Thus, there also is a need in the art to develop new therapeutic agents for treatment of chronic neurodegenerative disorders associated with HTLV-1 infection.

SUMMARY OF INVENTION

It is an object of the invention, therefore, to provide a method for inhibiting human T cell lymphotrophic virus type 1 replication in an infected cell.

It is another object of the invention to provide a method for inhibiting an effect of Tax 1 viral protein activity in a cell.

It is still another object of the invention to provide a method for treating a mammal infected with human T cell lymphotrophic virus type 1.

It is yet another object of the invention to provide a method for treating adult T cell leukemia associated with human T cell lymphotrophic virus type 1 infection.

It is still another object of the invention to provide a method for treating a chronic neurodegenerative disorder associated with human T cell lymphotrophic virus type 1 infection.

These and other objects of the invention are provided by one or more of the embodiments described below.

One embodiment of the invention provides a method for inhibiting human T cell lymphotrophic virus type 1 replication in a cell which comprises contacting the cell with a viral replication inhibiting amount of a protein kinase C inhibitor.

Another embodiment of the invention provides a method for inhibiting an effect of Tax 1 viral protein activity in a cell which comprises contacting the cell with a viral protein activity inhibiting amount of a protein kinase C inhibitor.

Yet another embodiment of the invention, provides a method for treating a mammal infected with human T cell lymphotrophic virus type 1 which comprises administering to the mammal a therapeutically effective amount of a protein kinase C inhibitor.

Still another embodiment of the invention provides a method for treating adult T cell leukemia associated with human T cell lymphotrophic virus type 1 infection which comprises administering to an adult in need of such treatment a therapeutically effective amount of a protein kinase C beta isozyme selective inhibitor.

Yet another embodiment of the invention provides a method for treating a chronic neurodegenerative disorder associated with human T cell lymphotrophic virus type 1 infection which comprises administering to the mammal a therapeutically effective amount of a protein kinase C beta isozyme selective inhibitor.

The present invention thus provides the art with compounds effective in treating HTLV-1 infection and the diseases associated therewith.

DETAILED DESCRIPTION OF THE INVENTION

It is a discovery of the present invention that the therapeutic use of a particular class of protein kinase C inhibitors, i.e., inhibitors of the $\beta$ isozyme of protein kinase C, and especially $\beta$ isozyme selective inhibitors of PKC, inhibits the induced effects of HTLV-1 viral protein activity and particularly viral replication. Consequently, such compounds can be used therapeutically to treat patients infected with HTLV-1 infection.

HTLV-1 replication comprises the multiplying of the HTLV-1 genome during productive infection and reactivation of latent infection. Reactivation of the integrated, latent HTLV genome, includes HTLV replication, e.g., forming multiple transcripts of the HTLV-1 genome, proper processing of HTLV-1 transcripts, HTLV-1 expression, e.g., translation of virus-specific proteins such as Tax 1, virus assembling, as well as releasing infectious HTLV-1 particles and HTLV-1 proteins.

HTLV-1 viral proteins such as Tax 1 exert their effects via interaction with the viral system as well as the host system. The induced effects of HTLV-1 viral protein activity include but are not limited to regulating transcription of the HTLV-1 virus as well as a variety of other cellular genes (Kwanyee et al., Nature 23: 776–778, 1988; Tan et al., Mol. Cell. Biol. 9: 1733–1745, 1989; and Yoshimura et al., EMBO J 9: 2537–2542, 1990). Tax 1 viral protein is secreted extracellularly by HTLV-1 infected cells (Lindholm et al., New Biol. 2: 1034–1043, 1990). The secreted extracellular Tax 1 can be taken up by surrounding cells and activates transcriptional factors such as NF-κB in the cells (Smith et al., J. Clin. Invest. 87: 761–766, 1991; Arima et al., J. Virology 65: 6892–6899, 1991). Cells infected with HTLV-1 have been shown to produce certain transriptional factors constitutively such as NF-κB (Lindholm et al., J. Virology 70: 2525–2532, 1996).

Individuals infected with HTLV-1 are prone to developing adult T cell leukemia (Poiesz et al., PNAS 77: 7415–7419, 1980; Hinuma et al., PNAS 78: 6476–6480, 1981). In addition, HTLV-1 infected individuals can manifest chronic neurodegenerative disorders such as tropical spastic paraparesis and myelopathy (Gessain et al., lancet II: 407–410, 1985, Osame et al., Lancet I: 1031–1032, 1986).

Though not wishing to be limited to any technical explanation, applicants believe that PKC affects HTLV-1 viral protein activity and thus viral replication. Viral protein Tax 1 diretly interacts with and activates PKC (Lindholm et al., J. Virology 70: 2525–2532, 1996). It has been demonstrated that some PKC inhibitors block Tax 1 induced activation of cellular proteins such as NF-κB in cells infected with HTLV-1 (Lindholm et al., J. Virology 70: 2525–2532, 1996). It also has been shown that PKC inhibition blocks the proper processing of HTLV-1 mRNA which is required for efficient viral replication (Adchi et al., Biochem. Biophys. Res. Commun. 169: 469–475, 1990). Further evidence supporting PKC's role in efficient replication of HTLV-1 is the ability of PKC inhibitors to decrease expression of bovine leukemia virus which is structurally and biologically similar to HTLV-1 (Jensen et al., J. Virology 66: 4427–4433, 1992). Therefore, PKC inhibitor compounds as described in the present invention can be used therapeutically to treat HTLV-1 infection and the diseases associated therewith both by suppressing the viral protein activity and especially by inhibiting viral replication.

The method of this invention preferably utilizes those protein kinase C inhibitors that effectively inhibit the β isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. Nos. 5,621,098, 5,552,396, 5,545,636, 5,481,003, 5,491,242, and 5,057,614, all incorporated by reference herein. Macrocyclic bis-indolylmaleimides are particularly represented by the compounds of formula I. These compounds, and methods for their preparation, have been disclosed in U.S. Pat. No. 5,552,396, which is incorporated herein by reference. These compounds are administered in a therapeutically effective amount to a human to inhibit the induced effects of HTLV-1 viral protein activity such as Tax 1 activity and to inhibit replication of HTLV-1, or to treat HTLV-1 infection. These compounds can also be administered to patients at risk of the disease conditions mentioned above as prophylactics.

One preferred class of compounds for use in the method of the invention has the formula (I):

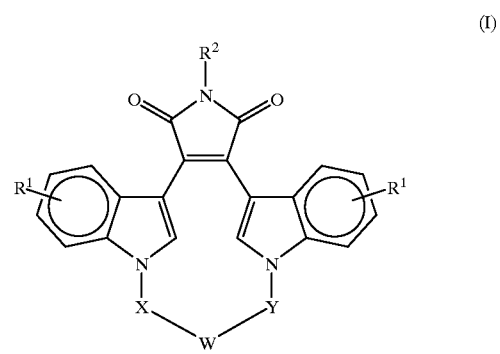

wherein:

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$-C$_4$ alkylene, substituted alkylene, or together X, Y, and W combine to form —(CH$_2$)$_n$—AA—;

R$^1$s are hydrogen or up to four optional substituents independently selected from halo, C$_1$-C$_4$ alkyl, hydroxy, C$_1$-C$_4$ alkoxy, haloalkyl, nitro, —NR$^4$R$^5$, or —NHCO(C$_1$-C$_4$ alkyl);

R$^2$ is hydrogen, CH$_3$CO—, —NH$_2$, or hydroxy;

R$^3$ is hydrogen, —(CH$_2$)$_m$aryl, —C$_1$-C$_4$ alkyl, —COO (C$_1$-C$_4$ alkyl), —CONR$^4$R$^5$, —(C=NH)NH$_2$, —SO (C$_1$-C$_4$ alkyl), —SO$_2$ (NR$^4$R$^5$), or —SO$_2$ (C$_1$-C$_4$ alkyl);

R$^4$ and R$^5$ are independently hydrogen, C$_1$-C$_4$ alkyl, phenyl, benzyl, or combine with the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug or ester thereof.

A more preferred class of compounds for use in this invention is represented by formula I wherein the moieties —X—W—Y— contain 4 to 8 atoms, which may be substituted or unsubstituted. Most preferably, the moieties —X—W—Y— contain 6 atoms.

Other preferred compounds for use in the method of this invention are those compounds of formula I wherein R$^1$ and R$^2$ are hydrogen; and W is a substituted alkylene, —O—, S—, —CONH—, —NHCO— or —NR$^3$—. Particularly preferred compounds for use in the invention are compounds of the formula Ia:

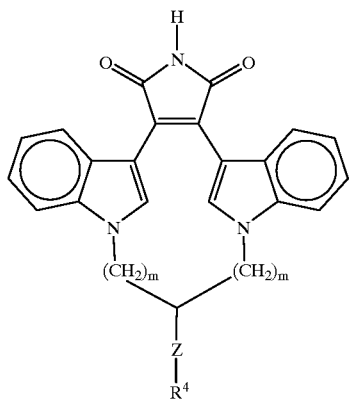

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$) (CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof. Most preferred compounds of the formula Ia are those wherein Z is CH$_2$; and R$^4$ is —NH$_2$, —NH(CF$_3$), or —N(CH$_3$)$_2$, or a pharmaceutically acceptable salt, prodrug or ester thereof.

Other preferred compounds for use in the method of the present invention are compounds wherein W in formula I is —O—, Y is a substituted alkylene, and X is an alkylene. These preferred compounds are represented by formula Ib:

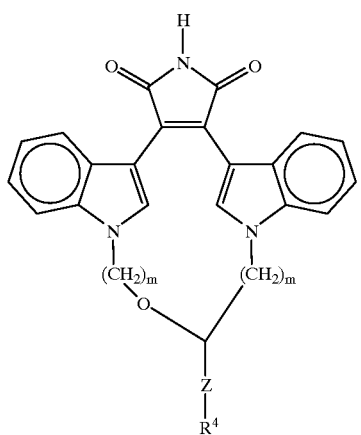

(Ib)

wherein Z is —(CH$_2$)$_p$—; R$^4$ is —NR$^5$R$^6$, —NH(CF$_3$), or N(CH$_3$)(CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof. Most preferred compounds of formula Ib are those wherein p is 1; and R$^5$ and R$^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfite, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs*, (1985).

The synthesis of various bis-indole-N-maleimide derivatives is described in Davis et al. U.S. Pat. No. 5,057,614 and the synthesis of the preferred compounds suitable for use in this invention are described in the previously identified U.S. Pat. Nos. 5,552,396 and in Faul et al. EP publication 0 657 411 A1, all of which are incorporated herein by reference.

One particularly preferred protein kinase-β inhibitor for use in the method of this invention is the compound described in Example 5g ((S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isoyme-selective, i.e., it is selective for the beta-1 and beta -2 isozymes. Other salts of this compound also would be favored, especially the mesylate salts.

A preferred mesylate salt can be prepared by reacting a compound of the formula II

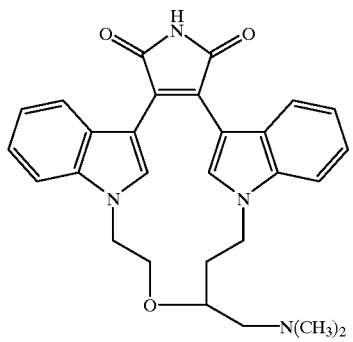

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by x-ray powder diffraction and can take from 5 minutes to 12 hours.

The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an x-ray diffraction pattern. Generally, the crystals have less than 10% amorphous solid and preferably less than 5% and most preferably less than 1% amorphous solid.

The mesylate salt is isolated by filtration or other separation techniques appreciated in the art, directly from the reaction mixture in yields ranging from 50% to 100%. Recrystallization and other purification techniques known in the art may be used to purify the salt further if desired.

One skilled in the art will recognize that a therapeutically effective amount of the protein kinase C inhibitor of the present invention is the amount sufficient to inhibit HTLV-1 replication or inhibit viral protein activity such as Tax 1. It is well within the ability of a person skilled in the art to measure HTLV-1 replication and viral protein activity such as Tax 1 activity. The amount administered varies inter alia, depending upon the concentration of the compound in the therapeutic formulation, and the body weight of the patient. Generally, an amount of protein kinase C inhibitor to be administered as a therapeutic agent for treating HTLV-1 infection will be determined on a case by case basis by the attending physician. As a guideline, the degree of infection, the strength of the immune system, the number of leukemic cells, the viral load, the body weight and age of the patient will be considered when setting an appropriate dose.

Generally, a suitable dose is one that results in a concentration of the protein kinase C inhibitor at the treatment site in the range of 0.5 nM to 200 μM, and more usually 0.5 nM to 200 nM. It is expected that serum concentrations of 0.5 nM to 20 nM should be sufficient in most circumstances.

To obtain these treatment concentrations, a patient in need of treatment likely will be administered between about 0.001 mg per day per kg of body weight and 50.0 mg per day per kg. Usually, not more than about 10.0 mg per day per kg of body weight of protein kinase C inhibitor should be needed. As noted above, the above amounts may vary on a case-by-case basis.

The effectiveness of the invention compounds can be evaluated in several experimental settings readily available in the art. The invention compounds can be tested on the growth and survival of cultured T cell lines derived from patients with adult T cell leukemia associated with HTLV-1 infection. The effects of the invention compounds also can be assessed on HTLV-1 viral replication in infected cells. The invention compounds can also be examined on the ability of viral protein such as Tax 1 to activate cellular transcriptional factors such as NF-κB in cultured cells. See Lindholm et al., J. Virology 70: 2525–2532, 1996, incorporated herein by reference. The ability of the invention compounds to attenuate the effects elicited by viral proteins such as Tax 1, to decrease viral replication, and/or to inhibit the growth of HTLV-1 infected T cells is predictive of beneficial clinical effect in patients suffering from HTLV-1 infection and the diseases associated therewith.

The compounds of formula I, and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystaline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 750 mg of the active ingredient. However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels.

Ointments generally are prepared using either (1) an oleaginous base, i.e., one consisting of fixed oils or hydrocarbons, such as white petrolatum or mineral oil, or (2). an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon concentration of compound in the formulation. Generally, the formulation will be applied to the effected tissue in an amount affording from about 1 to about 500 $\mu$g compound per $cm^2$ of an affected tissue. Preferably, the applied amount of compound will range from about 30 to about 300 $\mu g/cm^2$, more preferably, from about 50 to about 200 $\mu g/cm^2$, and, most preferably, from about 60 to about 100 $\mu g/cm^2$.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active agent | 5 |
| starch, dried | 200 |
| magnesium stearate | 10 |
| Total | 215 mg |

The above ingredients are mixed and filled into hard gelatin capsules in 460 mg quantities.

Formulation 2

A tablet is prepared using the ingredients below:

|  | Quantity (mg/capsule) |
| --- | --- |
| Active agent | 15 |
| cellulose, microcrystalline | 10 |
| silicon dioxide, fumed | 10 |
| stearic acid | 5 |
| Total | 40 mg |

The components are blended and compressed to form tablets each weighing 665 mg.

Formulation 3

Tablets each containing 60 mg of active ingredient are made as follows:

|  | Quantity (mg/tablet) |
|---|---|
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A method for inhibiting human T cell lymphotrophic virus type 1 replication in an infected cell which comprises contacting the cell with a viral replication inhibiting amount of an inhibitor of the β isozyme of protein kinase C.

2. The method of claim 1 wherein the inhibitor of the β isozyme of protein kinase C is a bis-indolylmaleimide or a macrocyclic bis-indolylmaleimide.

3. The method of claim 1 wherein the inhibitor is isozyme selective and where the isozyme selectivity is selected from the group consisting of beta-1 and beta-2 isozymes.

4. The method of claim 3 wherein the protein kinase C inhibitor has the following formula:

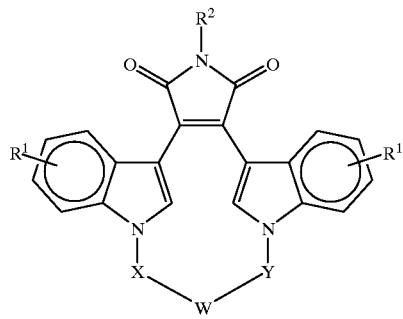

(I)

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy;

R$^3$ is hydrogen, (CH$_2$)$_m$aryl, C$_1$–C$_4$ alkyl, —COO(C$_1$–C$_4$ alkyl), —CONR$^4$R$^5$, —(C=NH)NH$_2$, —SO(C$_1$–C$_4$ alkyl), —SO$_2$ (NR$^4$R$^5$), or —SO$_2$ (C$_1$–C$_4$ alkyl);

R$^4$ and R$^5$ are independently hydrogen, C$_1$–C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

5. The method of claim 4 wherein the protein kinase C inhibitor has the following formula:

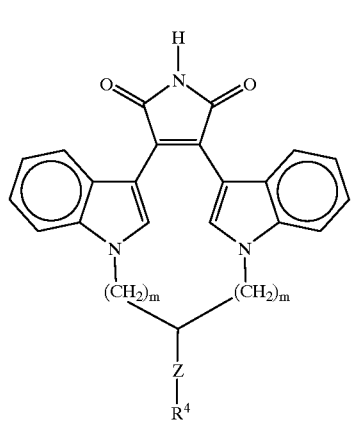

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof.

6. The method of claim 4 wherein the protein kinase C inhibitor has the following formula:

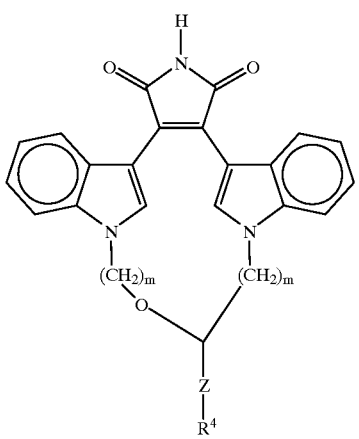

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof.

7. The method of claim 4, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its pharmaceutically acceptable acid salt.

8. A method of claim 7, wherein the pharmaceutically acceptable acid salt is selected from the hydrochloride salt and the mesylate salt.

9. A method for inhibiting an effect of Tax 1 viral protein activity in a cell which comprises contacting the cell with an viral protein activity inhibiting amount of an inhibitor of the β isozyme of protein kinase C.

10. The method of claim 9 wherein the inhibitor of the β isozyme of protein kinase C is a bis-indolylmaleimide or a macrocyclic bis-indolylmaleimide.

11. The method of claim 9 wherein the inhibitor is isozyme selective and where the isozyme selectivity is selected from the group consisting of beta-1 and beta-2 isoymes.

12. The method of claim 11 wherein the protein kinase C inhibitor has the following formula:

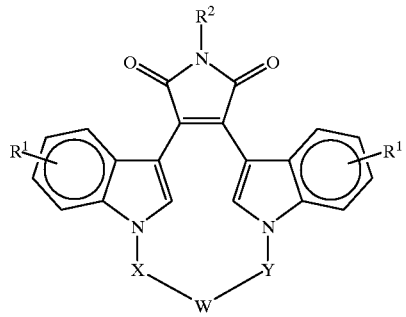

(I)

wherein:
W is —O—, —S—, —SO—, —SO$_2$—, —CO—, C$_2$–C$_6$ alkylene, substituted alkylene, C$_2$–C$_6$ alkenylene,
-aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, NR$^4$R$^5$, or —NHCO(C$_1$–C$_4$ alkyl);

R$^2$ is hydrogen, CH$_3$CO—, NH$_2$, or hydroxy;

R$^3$ is hydrogen, (CH$_2$)$_m$aryl, C$_1$–C$_4$ alkyl, —COO(C$_1$–C$_4$ alkyl), —CONR$^4$R$^5$, —(C=NH)NH$_2$, —SO(C$_1$–C$_4$ alkyl), —SO$_2$(NR$^4$R$^5$), or —SO$_2$(C$_1$–C$_4$ alkyl);

R$^4$ and R$^5$ are independenty hydrogen, C$_1$–C$_4$ alkyl, phenyl benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

13. The method of claim 12 wherein the protein kinase C inhibitor has the following formula:

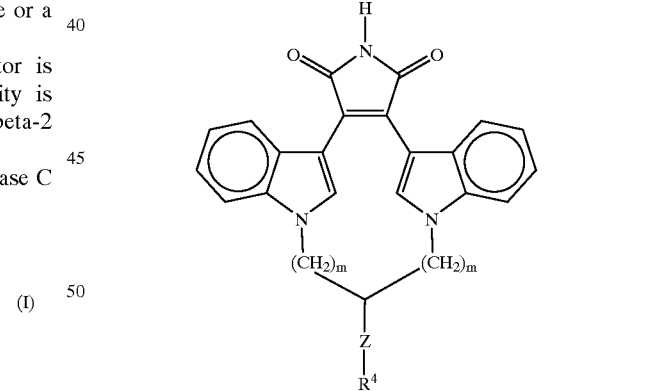

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof.

14. The method of claim 12 wherein the protein kinase C inhibitor has the following formula:

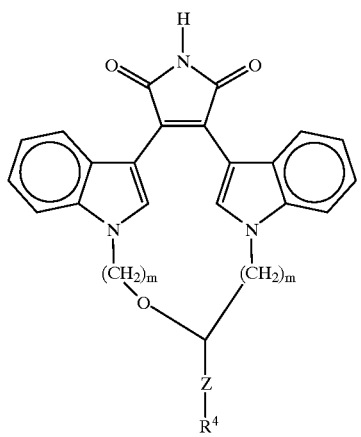

(Ib)

wherein Z is —(CH₂)ₚ—; R⁴ is —NR⁵R⁶, —NH(CF₃), or —N(CH₃)(CF₃); R⁵ and R⁶ are independently H or C₁–C₄ alkyl; p is 0, 1, or 2; and m is independently 2 or 3, or a pharmaceutically acceptable salt, prodrug or ester thereof.

15. The method of claim 12, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its pharnaceutically acceptable acid salt.

16. A method of claim 15, wherein the pharmaceutically acceptable acid salt is selected from the hydrochloride salt and the mesylate salt.

17. A method for treating a mammal infected with human T cell lymphotrophic virus type 1, which comprises administering to the mammal a therapeutically effective amount of an inhibitor of the β isozyme of protein kinase C.

18. The method of claim 17 wherein the inhibitor of the β isozyme of protein kinase C is a bis-indolylmaleimide or a macrocyclic bis-indolylmaleimide.

19. The method of claim 17 wherein the inhibitor is isozyme selective and where the isozyme selectivity is selected from the group consisting of beta-1 and beta-2 isozymes.

20. The method of claim 19 wherein the protein kinase C inhibitor has the following formula:

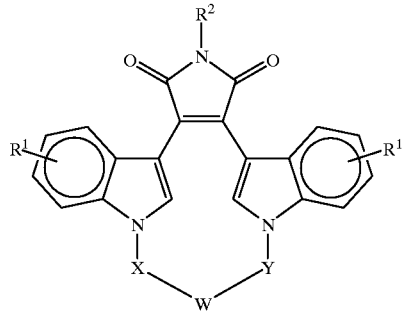

(I)

wherein:
W is —O—, —S—, —SO—, —SO₂—, —CO—, C₂–C₆ alkylene, substituted alkylene, C₂–C₆ alkenylene, -aryl-, -aryl(CH₂)ₘO—, -heterocycle-, -heterocycle-(CH₂)ₘO—, -fused bicyclic-, -fused bicyclic-(CH₂)ₘO—, —NR³—, —NOR³—, —CONH—, or —NHCO—;

X and Y are independently C₁–C₄ alkylene, substituted alkylene, or together X, Y, and W combine to form —(CH₂)ₙ—AA—;

R¹s are hydrogen or up to four optional substituents independently selected from halo, C₁–C₄ alkyl, hydroxy, C₁–C₄ alkoxy, haloalkyl, nitro, NR⁴R⁵, or —NHCO(C₁–C₄ alkyl);

R² is hydrogen, CH₃CO—, NH₂, or hydroxy;

R³ is hydrogen, (CH₂)ₘaryl, C₁–C₄ alkyl, —COO(C₁–C₄ alkyl), —CONR⁴R⁵, —(C=NH)NH₂, —SO(C₁–C₄ alkyl), —SO₂ (NR⁴R⁵), or —SO₂ (C₁–C₄ alkyl);

R⁴ and R⁵ are independently hydrogen, C₁–C₄ alkyl, phenyl benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

21. The method of claim 20 wherein the protein kinase C inhibitor has the following formula:

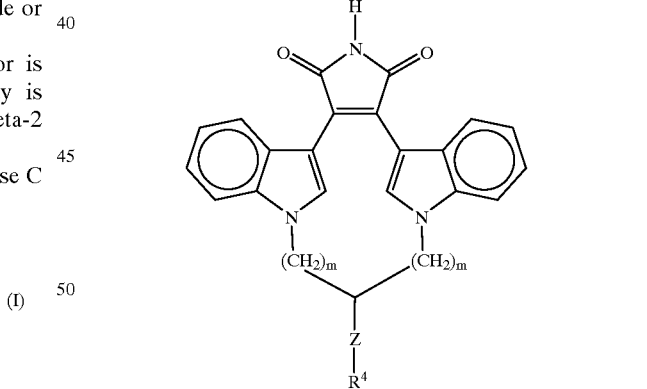

(Ia)

wherein Z is —(CH₂)ₚ— or —(CH₂)ₚ—O—(CH₂)ₚ—; R⁴ is hydroxy, —SH, C₁–C₄ alkyl, (CH₂)ₘaryl, —NH(aryl), —N(CH₃)(CF₃), —NH(CF₃), or —NR⁵R⁶; R⁵ is hydrogen or C₁–C₄ alkyl; R⁶ is hydrogen, C₁–C₄ alkyl or benzyl; p is 0, 1, or 2; and m is independently 2 or 3, or a pharmaceutically acceptable salt, prodrug or ester thereof.

22. The method of claim 20 wherein the protein kinase C inhibitor has the following formula:

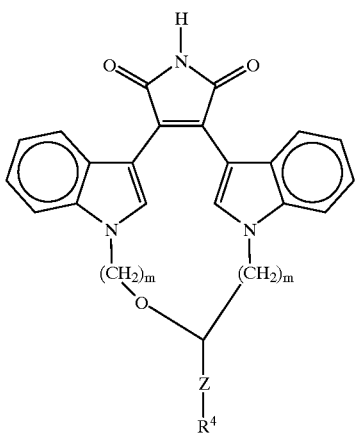

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof.

23. The method of claim 20, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its pharmaceutically acceptable acid salt.

24. A method of claim 23, wherein the pharmaceutically acceptable acid salt is selected from the hydrochloride salt and the mesylate salt.

25. A method for treating adult T cell leukemia associated with human T cell lymphotrophic virus type 1 infection, which comprises administering to an adult in need of such treatment a therapeutically effective amount of an inhibitor of the β isozyme of protein kinase C.

26. A method for treating a chronic neurodegenerative disorder associated with human T cell lymphotrophic virus type 1 infection, which comprises administering to a mammal in need of such treatment a therapeutically effective amount of an inhibitor of the β isozyme of protein kinase C.

27. The method of claim 26, wherein the chronic neurodegenerative disorder is selected from the group consisting of tropical spastic paraparesis and myelopathy.

* * * * *